US00PP07772P

United States Patent [19]

Spooner

[11] Patent Number: Plant 7,772

[45] Date of Patent: Jan. 21, 1992

[54] MINIATURE ROSE PLANT NAMED 'SPOMAUR'

[76] Inventor: Raymond A. Spooner, 8285 SW. 185th Ave., Beaverton, Oreg. 97007

[21] Appl. No.: 538,430

[22] Filed: Jun. 15, 1990

[51] Int. Cl.[5] ..... A01H 5/00
[52] U.S. Cl. ..... Plt./10
[58] Field of Search ..... Plt./10, 7

*Primary Examiner*—Howard J. Locker

[57] ABSTRACT

The present invention relates to a new and distinct variety of rose plant of the miniature rose class named 'Spomaur'. It is characterized particularly by its clear non-fading crimson red petal coloration, occasional white streaks on the outer two or three petals, high-centered bloom, and reflexing or recurling nature of the petals.

1 Drawing Sheet

The present invention relates to a new and distinct variety of rose plant of the miniature rose class. Among the novel and distinguishing characteristics which distinguish this new variety (varietal denomination 'Spomaur') from all other varieties of which I am aware are its clear crimson red blooms, occasional white streaks on the outer two or three petals, the flowers being high centered and petals recurling as the flower slowly opens. The blooms are borne singly and also in clusters of five to eight blooms per stem. The flowers are long lasting on the plant and maintain their color well upon aging, even in hot weather. The plant has a vigorous, bushy, much branched, upright growth habit and is easy to propagate.

The color and bud form are generally similar to the pollen parent 'Centerpiece' with the main difference being that 'Centerpiece' has white tint showing at the base of the petals.

Asexual reproduction by budding and by cuttings of the new variety as performed in Washington County, Oreg., have shown that the foregoing and other distinguishing characteristics of same come true to form and are established and transmitted faithfully through succeeding propagations.

BRIEF DESCRIPTION OF THE DRAWING (PHOTOGRAPH)

The accompanying photograph shows typical specimens of the vegetative growth and flowers of the new variety in different stages of development. The color depictions set forth therein are as nearly true as it is reasonably possible in a color illustration of this character.

The following is a detailed description of my new variety, with color terminology in accordance with the Royal Horticultural Society Colour Chart (R.H.S.C.C.). The terminology used in color description herein refers to plate numbers in the aforementioned color chart. "137B" is plate 137B of the Royal Horticultural Society Colour Chart.

Parentage:

*Seed parent.*—A seedling resulting from crossing 'Prominent' (U.S. Plant Pat. No. 3,380) and 'Zinger' (U.S. Plant Pat. No. 4,293).

*Pollen parent.*—'Centerpiece' (not patented).

Class: Miniature.

The following observations are made of specimens grown out doors in Washington County, Oreg., during July.

FLOWER

Blooming habit: Nearly continuous.

A. Bud:
- (1) *Size.*—About 2½ cm in length.
- (2) *Form.*—Pointed.
- (3) *Color.*—Both sides of petals are crimson red color 45-A.
- (4) *Sepals.*—Permanent, spear shaped, reflexed.
- (5) *Peduncle.*—Length — about 3½ cm. Aspect — straight. Strength — erect. Color — near 137C green.

B. Bloom:
- (1) *Size.*—When fully expanded — about 4½ cm in diameter.
- (2) *Borne.*—Singly or in sprays of five to eight blooms.
- (3) *Form.*—Urn shaped and very double.
- (4) *Petalage.*—About 50 under normal conditions.
- (5) *Color.*—Crimson red color 45-A. The color holds during the duration of bloom which is about one week.

C. Petals:
- (1) *Texture.*—Moderately thick and of good substance.
- (2) *Appearance.*—Velvety, both inside and outside.
- (3) *Form.*—The bloom has imbricated form and reflexes. Both inner and outer petals are pointed and reflex smoothly.
- (4) *Arrangement.*—Regularly arranged.
- (5) *Petaloids in center.*—Medium, surrounding center.
- (6) *Persistence.*—Drop off cleanly.
- (7) *Fragrance.*—Moderate.
- (8) *Lasting quality.*—Long lasting on plant and cut blooms. This period is about a week.

REPRODUCTIVE ORGANS

A. Stamens, filaments and anthers:
- (1) *Arrangement.*—Regularly arranged stamens around low pistils.
- (2) *Color.*—Medium yellow.

B. Pollen:
- *Color.*—Yellow.

C. Styles:

*Even length.*—Introse.

D. Stigmas:

*Color.*—Medium yellow.

E. Hips: About 1 cm.

F. Sepals: Permanent, spear shaped, reflexed.

PLANT

A. Form: Bushy, rounded.

B. Growth: Uniform branching, medium vigor, height 36 cm.

C. Foliage: Normally 5 leaflets, occasionally 3 leaflets.

(1) *Size.*—1½ cm leaflets.

(2) *Quantity.*—Abundant.

(3) *Color.*—New foliage — red, maturing to 137B green.

(4) *Shape.*—Oval pointed, supported by short petiolule.

(5) *Texture.*—Glossy.

(6) *Edge.*—Serrated.

(7) *Serration.*—Serrulate.

(8) *Leaf stem.*—Color — green 137B, turning green 138B.

(9) *Stipules.*—Slightly bearded.

(10) *Rachis.*—Medium green in color, upper side grooved.

(11) *Resistance to disease.*—Blackspot — Average. Mildew — Average. Rust — Average.

D. Wood:

(1) *New wood.*—Color — Light green 137B. Bark — smooth.

(2) *Old wood.*—Color — Green 138B, Bark — smooth with sturdy growth 3 cm internodes.

E. Thorns:

*Quantity.*—Main stalk — average, and laterals from stalk — average.

*Form.*—Dilated at base and declining.

*Length.*—⅓ cm.

*Color.*—Rose, turning brown at maturity.

*Position.*—Ordinary.

*Prickles.*—Average.

F. Winter hardiness: Requires ordinary protection in extreme climates.

I claim the following:

1. A new and distinct variety of miniature rose plant named 'Spomaur' substantially as herein described and illustrated, being characterized particularly by its clear non-fading crimson red petal coloration, white streaks on the outer two or three petals, high-centered bloom, and reflexing petals.

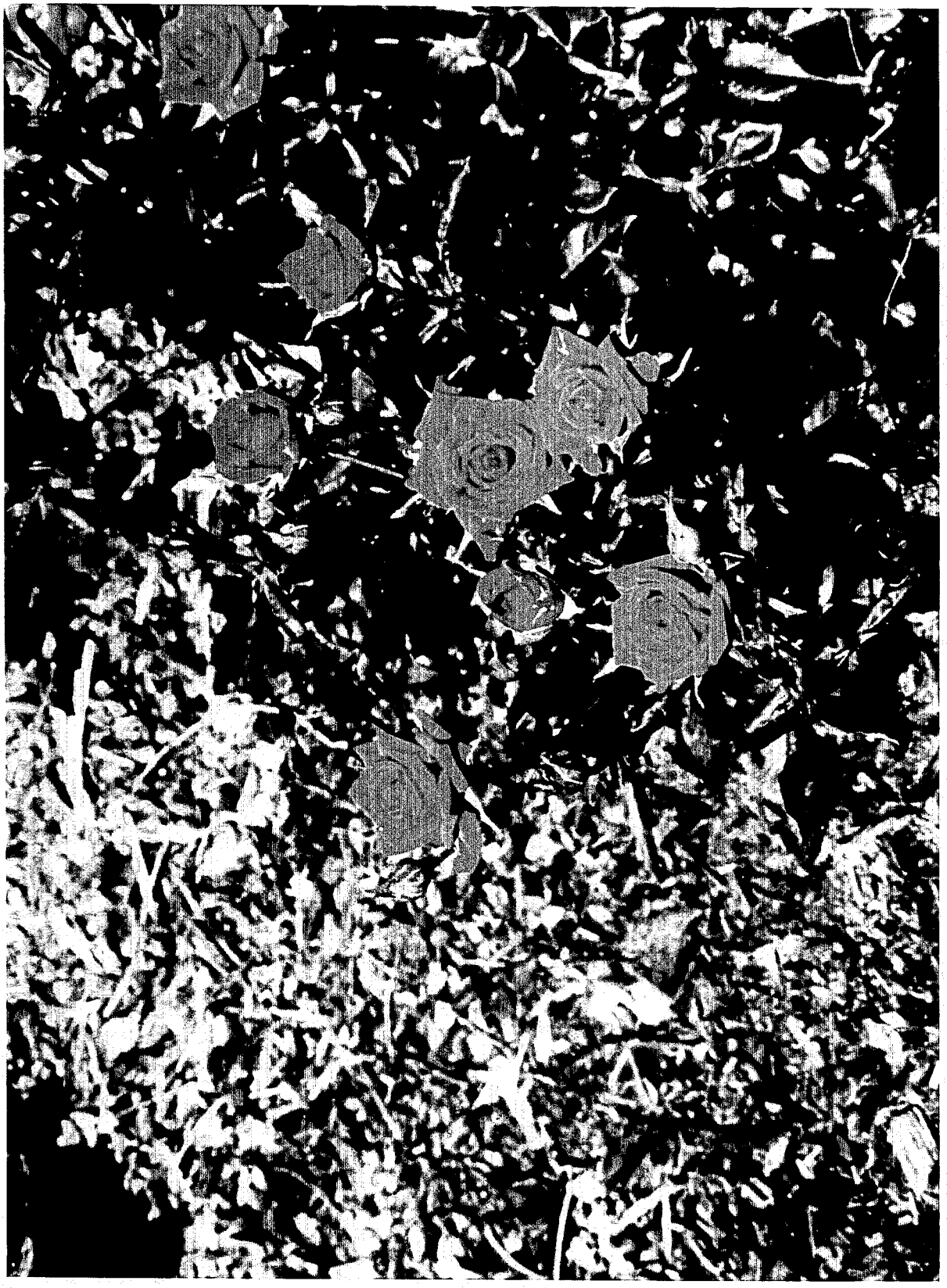

* * * * *